(12) United States Patent
Allford et al.

(10) Patent No.: US 11,457,984 B1
(45) Date of Patent: Oct. 4, 2022

(54) SURGICAL PROCESS FOR KNEE REPLACEMENT AND KNEE RESURFACING PROCESS THEREFOR

(71) Applicant: ARC SPECIALTIES, INC., Houston, TX (US)

(72) Inventors: Daniel Allford, Houston, TX (US); Kevin Sevcik, Houston, TX (US); Stefan W. Kreuzer, Houston, TX (US)

( * ) Notice: Subject to any disclaimer, the term of this patent is extended or adjusted under 35 U.S.C. 154(b) by 364 days.

(21) Appl. No.: 16/700,527

(22) Filed: Dec. 2, 2019

(51) Int. Cl.
  *A61B 17/00* (2006.01)
  *A61B 34/32* (2016.01)
  *A61B 17/16* (2006.01)
  *A61B 34/10* (2016.01)

(52) U.S. Cl.
  CPC .......... *A61B 34/32* (2016.02); *A61B 17/1675* (2013.01); *A61B 2034/105* (2016.02)

(58) Field of Classification Search
  CPC combination set(s) only.
  See application file for complete search history.

(56) References Cited

U.S. PATENT DOCUMENTS

| | | | |
|---|---|---|---|
| 6,837,892 B2 | 1/2005 | Shoham | |
| 7,742,801 B2 | 6/2010 | Neubauer | |
| 8,498,744 B2 | 7/2013 | Odermatt | |
| 8,679,125 B2 | 3/2014 | Smith | |
| 10,034,675 B2 | 7/2018 | Pack | |
| 10,045,826 B2 | 8/2018 | Abbasi | |
| 10,085,804 B2 | 10/2018 | Nortman | |
| 10,123,839 B2 | 11/2018 | Netravali | |
| 2017/0202620 A1 | 7/2017 | Shalayev | |
| 2017/0360513 A1 | 12/2017 | Amiot | |
| 2021/0192759 A1* | 6/2021 | Lang | A61B 34/10 |

* cited by examiner

*Primary Examiner* — Sameh R Boles
(74) *Attorney, Agent, or Firm* — Egbert, McDaniel & Swartz, PLLC; John S. Egbert; Kevin W. McDaniel (57) ABSTRACT

A knee resurfacing process has the steps of fixing a bone in a position, creating an incision in a knee so as to expose a surface of the knee, guiding a probe of a robot arm around the perimeter of a search zone on the surface of the knee, probing the probe of the robot arm onto the knee so as to define a plurality of points within the perimeter, collecting point cloud data from the plurality of points so as to form an image of the probed surface, and shaping the knee relative to the collected point cloud data. The step of guiding is hand guiding the probe so that the probe penetrates tissues at a bony surface of the knee and contacts the bone of the knee. A force of the contact of the probe with the bone of the knee is measured.

12 Claims, 5 Drawing Sheets

SURGICAL PROCESS FOR KNEE REPLACEMENT AND KNEE RESURFACING PROCESS THEREFOR

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to knee replacement processes. More particularly, the present invention relates to the resurfacing of the knee for the purpose of receiving an implant thereon. More particularly, the present invention relates to robotic surgery wherein the robotic arm is used for the resurfacing of a knee.

2. Description of Related Art Including Information Disclosed Under 37 CFR 1.97 and 37 CFR 1.98

Knee replacement, also known as knee arthroplasty, is a surgical procedure to replace the weight-bearing surfaces of the knee joint to relieve pain and disability. It is most commonly performed for osteoarthritis, and also for other knee diseases, such as rheumatoid arthritis and psoriatic arthritis. Knee replacement surgery can be formed as a partial or a total knee replacement. In general, the surgery consists of replacing the diseased or damaged joint surfaces of the knee with metal and plastic components shaped to allow continued motion of the knee.

In the pre-operative preparation of the past, radiographic classification and severity of symptoms need to be assessed. The radiography should consist of weight-bearing X-rays of both knees—AP, lateral and 30° of flexion. Full length projections are also used in order to adjust the prosthesis to provide a neutral angle for the distal lower extremity. Two angles that are used for this purpose are: (1) the hip-knee-shaft angle, which is the angle formed between a line through the longitudinal axis of the femoral shaft and its mechanical axis, which is a line from the center of the femoral head to the intercondyal notch of the distal reamer; and (2) the hip-knee-ankle angle which is an angle between the femoral mechanical axis and the center of the ankle joint.

The surgery involves exposure of the front of the knee, with detachment of part of the quadriceps muscle (the vastus medialis) from the patella. The patella is displaced one side of the joint so as to allow exposure of the distal end of the femur and the proximal end of the tibia. The ends of the bones are then cut to shape using cutting guides oriented to the longitudinal axis of the bones. The cartilages and the anterior cruciate ligament are removed. The posterior cruciate ligament may also be removed. The tibial and fibular collateral ligaments are preserved. Metal components are then impacted onto the bone or fixed using polymethylmethacrylate cement. Alternative techniques exist that affix the implant without cement. The cement-less techniques may involve osseo integration, using porous metal prostheses. Finally, stability and range of motion is checked, followed by irrigation, hemostasis, placement of hemovacs, and closure.

For the femoral replacement, a round-ended implant is used for the femur. This mimics the natural shape of the joint. The component on the tibia is flat, although sometimes it has a stem which goes down inside the bone for further stability. A flattened or slightly dished height density polyethylene surface is then inserted onto the tibial component so that the weight is transferred metal-to-plastic and not metal-to-metal.

In one category of total knee prostheses, the articular surface of the distal femur and proximal tibia are resurfaced with respect to metal and plastic condylar-type articular bearing components. These knee prostheses provide adequate rotational and translational freedom and require minimal bone resection to accommodate the components within the boundaries of the available joint space. The patella-femoral joint may also be resurfaced by a third prosthetic component, as well. The femoral, tibial and patella prosthetic resurfacing components are affixed to respective surgically-prepared adjacent bone structures by cementing or by biological bone ingrowth fixation means.

The femoral component is a metal alloy construction (i.e. a cobalt-chrome alloy) and provides medial and lateral condylar bearing surfaces of the multi-radius design of similar shape in geometry as the natural distal femur or femoral-side of the knee joint. The tibial component can be made entirely of plastic or can be comprised of a metallic base component and an interlocking plastic component. The plastic tibial plateau bearing surfaces are of concave multi-radius geometry to more or less match the articular geometry of the mating femoral condyles, depending on the desired design mechanics of the primary femoro-tibial motion. In the resurfacing type of total knee prosthesis, both the femoral and tibial components are positioned on the respective sides of the knee joint and are not mechanically connected or linked together.

Additionally, in resurfacing types of total knee prostheses, the tibial plateau bearing surface geometry can assume a variety of configurations, depending upon the desired extent of articular contact congruency and associated translational and rotational secondary femoro-tibial motions. These various secondary motions allow the resurfaced knee to function in a natural-like biomechanical manner in conjunction with the surrounding ligamentous and muscle structures about the knee joint. The viable soft tissue structures functionally maintain the femoral and tibial bearing surfaces in contact so as to provide the necessary levels of constraining force to achieve knee joint stability and to decrease the principle motion in flexion-extension and secondary motions in a controlled manner. Additionally, this functional interaction between the surrounding tissue structures in the implanted knee prosthesis minimizes abrupt motion stoppage or impact loading to properly design prosthetic articular surfaces, and thus prevents overstressing at the component fixation interface.

Figure 1:
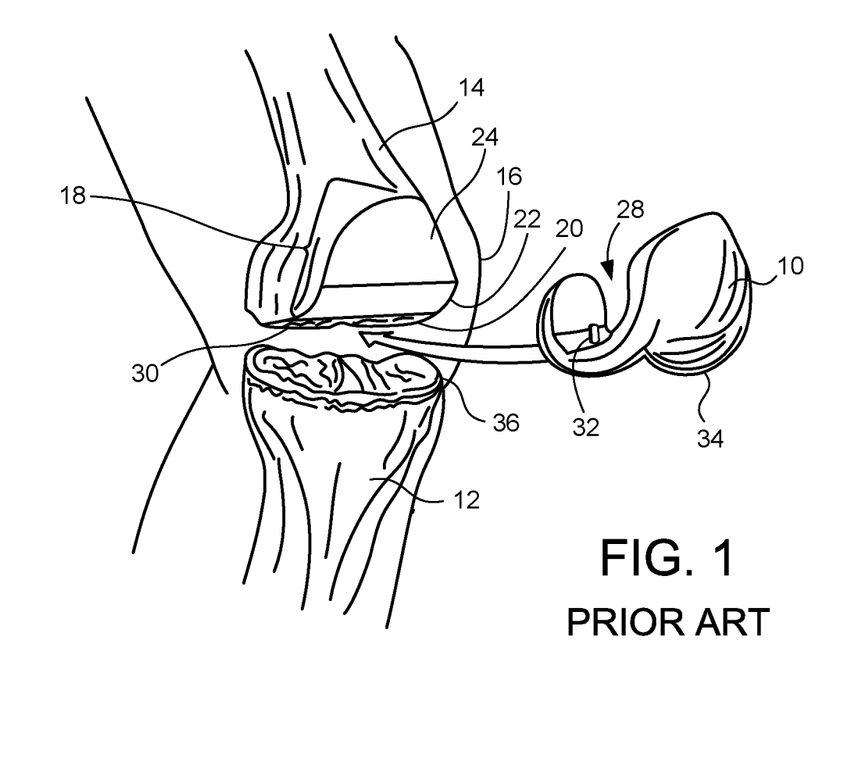
FIG. 1 exploded perspective view of a prior art knee replacement system.

FIG. 1 shows a prior art type of knee replacement. In particular, the knee prosthesis 10 is particularly illustrated. The knee prosthesis 10 is to be placed between the tibial component 12 and the femoral component 14 of the knee 16. In particular, in order to accommodate the prosthesis 10, the femoral surface 18 is removed. The femoral surface 18 has at least a first planar surface 20, a second planar surface 22 and a third planar surface 24. These planar surfaces 20, 22 and 24 are intended to accommodate the respective planar surfaces within the notch 28 of the prosthetic component 10. As such, the prosthetic component 10 can be received by the femoral component 14. It should be noted that holes 30 are formed on the first planar surface 20. Holes 30 are intended to accommodate pins 32 located within the notch 28 of the prosthetic component 10. Once the prosthetic component 10 is installed, the outer surface 34 will bear against the tibia 12 or against an implant pad 36 affixed to the upper end of the tibia 12.

Figure 2:
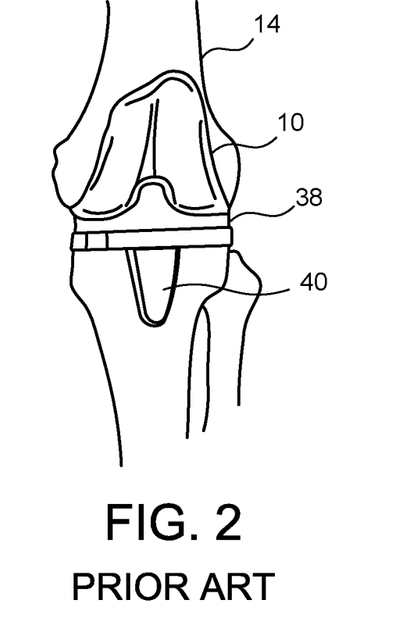
FIG. 2 is a frontal view showing the prior art procedure for installation of the prosthetic component onto the femoral surface.

FIG. 2 shows the assembly of the prosthetic component 10 onto the femoral component 14. Ultimately, there is a plastic insert 38 that is positioned on the tibial component 40.

Figure 3:
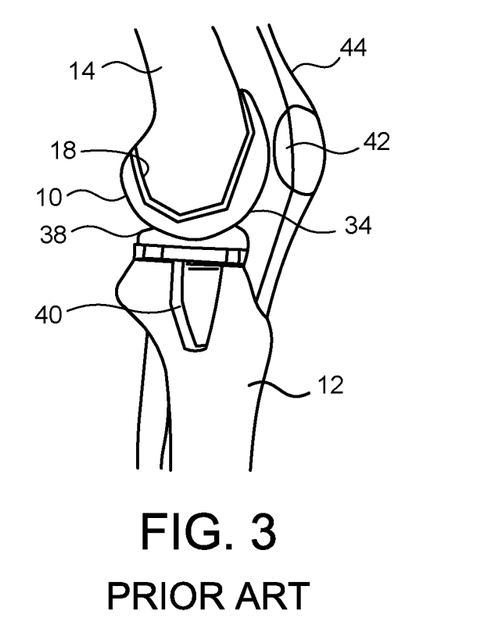
FIG. 3 is a cross-sectional side view showing a prior art procedure for the installation of they prosthetic component onto the femoral surface in relation to the tibia.

FIG. 3 shows a side view wherein the prosthetic component 10 is affixed to the femoral surface 18 of the femur 14. The notch 28 of the prosthetic component 10 has a plurality of planar surfaces which match the planar surfaces formed on the femoral surface 18. The plastic insert 38 bears against the outer surface 34 of the prosthetic component 10. The tibia component 40 is affixed to the upper end of the tibia 12 and also bears against the plastic insert 38. A patella button 42 can be affixed to the patella tendon 44 in this procedure of the prior art.

A major problem with the prior art shown in FIGS. 1-3 is the ability to accurately form the femoral surface 18. Typically, a large amount the CT and MRI imaging is used so as to provide the surgeon with a visualization of the femoral surface 18. The surgeon will then use a variety of milling tools or shaping tools in order to form the planar surfaces 20, 22 and 24 (along with any other surfaces). As such, at best, the surgical procedure is carried out with a large degree of guesswork based on experience. Measurements can be taken during the shaping process so as to allow the surgeon to approximate the shape of the surfaces within the notch 28 of the prosthetic component 10. As a result, there is often a relatively imperfect fit between the prosthetic component 10 and the femoral surface 18. Whenever there is an imperfect fit, the stability between the prosthetic component 10 and the femoral surface 18 will be unstable. In other circumstances, the CT scan or the MRI scan will be imperfect. This imperfect imaging can be from the nature of the imaging that is carried out or as a result of the various tissues surrounding the femoral surfaces 18. Whenever an inaccurate image is obtained, it becomes more difficult for the surgeon to carry out the necessary shaping of the femoral surfaces 18. As such, a need has developed so as to more accurately form the planar surfaces 20, 22 and 24 at the femoral surface 18 of the femur 10.

In other circumstances, when the prosthetic component 10 does not accurately fit the shaped femoral surface 18, then additional surgical procedures will be required so as to establish a proper fit. If the shaped femoral surface 18 is too large for the prosthetic component 10, either a larger prosthetic component will be required or additional procedures will be required so as to reduce the size of the femoral surface 18. If the shaped femoral surface 18 is too small for the prosthetic component 10, then the only solution is to find a smaller prosthetic component. As can be appreciated, all of these procedures greatly increase the complexity and time of the surgical procedure. Ultimately, the result of all of these procedures would be that there is an improper fit between the femoral surfaces 18 and the prosthetic component 10. Whenever an improper fit occurs, there is possibility of instability, damage to the femoral surfaces 18, or more frequent future replacement.

In the past, various patents have issued relating to robot-assisted surgery. For example, U.S. Pat. No. 6,837,892, issued on Jan. 4, 2005 to M. Shoham, discloses a miniature surgical robot. This robot attaches directly to the bone of a patient. Two-dimensional X-ray images of the robot on the bone are registered with three-dimensional images of the bone. This locates the robot on the bone of the patient. The robot is then directed to pre-operative determined positions based upon a pre-operative plan by the surgeon. The robot then moves to the requested surgical site and aligns a sleeve through which the surgeon can insert a surgical tool.

U.S. Pat. No. 7,742,801, issued on Jun. 22, 2010 to Neubauer et al., discloses a planning method and system for free-form implant modification. This method for planning a bone implant ascertains a condition of a bone to be treated and identifies a dysfunctional part of the bone. A free-form area can then be ascertained and registered. The free-form area lies below the dysfunctional part. A control data set then is produced that forms the basis for ablating the bone on the ascertained free-form area.

U.S. Pat. No. 8,498,744, issued Jul. 30, 2013 to Odermatt et al., teaches a surgical robotic system that provides a combination of programmed control when a high degree of accuracy is required, and manual control when a high degree of accuracy is not required. The surgical robot system includes a robotic arm, a tool coupled to the robotic arm, and a controller programmable to be switched between an at least partial manual control mode and an at least partial program control mode. In the partial program control mode, the controller is programmed to generate control signals that will limit movement or operation of the tool away from a programmed course. In the manual control mode, the controller is programmed to allow the tool to move and operate away from the program course without imposing resistance to the movement or operation of the tool.

U.S. Pat. No. 8,679,125, issued on Mar. 25, 2014 to Smith et al., discloses a method of performing hip surgery with a robotic-guided system. This method includes identifying 9 femoral acetabular impingement on the patient. Data related to a proximal femur and acetabulum of the patient is required. t three-dimensional model of at least one of the patient's proximal femur and acetabulum is created based on the data acquired. The location and amount of bone to be removed are determined. Dynamic movement limits of a cutting tool associated with the robotic guided system is set based on the determination. The determined bone of at least one of the proximal femur and acetabulum is removed with a tool while being inhibited from moving the tool outside the dynamic limit by the robotic guided system.

U.S. Pat. No. 10,123,839, issued on Nov. 13, 2018 to N. A. Netravali, shows a system and process for pre-operative planning and precise bone removal for femoral acetabular impingement. This process includes receiving an image of the bone, creating a three-dimensional model of the bone, and determining the location of the bone such that a precise orientation is known. Software is used to automatically generate a volume of the bone to be removed. Robotically-controlled milling is automatically performed to remove the impingement of the bone. A simulated kinematic analysis of the motion of the bone is carried out after the bone is removed. The process can further include the step of receiving an input from the user, manually determined by the user, based upon three dimensional models of the bone, to modify a volume of the bone to be removed.

U.S. Pat. No. 10,034,675, issued on Jul. 31, 2018 to Pack et al., teaches a method and system to optimize ligament reconstruction surgical outcomes by enabling bone tunnels to be precisely and optimally placed through the use of pre-operative planning systems coupled with precision control bone evacuation machines. The method includes receiving and processing scan data of the patient's bone, pre-determining the optimal tunnel placement parameters with the scanned data, placing registration markers on the patient's bone percutaneously, and creating a tunnel in the patient's bone with a system coupled to receive and execute according to pre-determined optimal tunnel placement parameters.

U.S. Pat. No. 10,045,826, issued on Aug. 14, 2018 to Abbassi et al., provides a system and method for repairing bone with multiple tools. This method includes superimposing a first virtual boundary on a virtual bone and superimposing a second virtual boundary on the virtual bone. The method further includes robotically modifying the bone of the patient with a planar tool along with a first working boundary to create a first surface. The first working boundary may correspond to the first virtual boundary. The method further includes robotically modifying the bone of the patient with a rotary tool along a second working boundary to create a second surface. The second working boundary corresponds to the second virtual boundary.

U.S. Pat. No. 10,085,804, issued on Oct. 2, 2018 to Nortman et al., discloses a robotic system for preparing a bone to receive a prosthetic device. The robotic system includes a controllable guide structure configured to guide cutting of the bone into a shape for receiving the prosthetic device and a computer readable medium for storing data representative of the prosthetic device. The prosthetic device includes a body portion having an implementation surface configured to face the bone upon implantation, and at least one feature that provides a constraint structure that will constrain the prosthetic device in the bone. The robotic system includes a control system for controlling the guide structure and which is configured to define at least one bone-cutting pattern for removing a first portion of the bone in a first area sufficient to seat the body portion.

U.S. Patent Application Publication No. 2017/0202620, published on Jul. 20, 2017 to Shalayev et al., shows a process for creating a curved contour on or within a bone. The process includes positioning a bone of the patient in a fixed position in a coordinate system, generating scan data of the bone, creating a three-dimensional surface model of the bone based on the scanned data, generating a cutting program to modify a surface of the bone based on the three-dimensional surface model and a prosthesis having a bone interface shape that is complementary to the curved contour, and modifying the bone with one or more curved blades on a curved drill bit that is robotically driven and positioned with the cutting program to form the curved contour.

U.S. Patent Application Publication No. 2017/0360513, published on Dec. 21, 2007 to Amiot et al., provides a robotized system for femoral acetabular impingement resurfacing. A femoral acetabular impingement resurfacing controller is used to perform detecting and resurfacing of the femoral acetabular impingement. This resurfacing controller may include a bone model generator receiving bone imaging and generating a model of at least one osteophyte and of a surface of a native bone surrounding the one osteophyte. The resurfacing controller has an osteophyte identifier to set a virtual three-dimensional boundary surface between the native bone surface and the osteophyte. The resurfacing controller can include a resurfacing navigator to generate an output navigation file. The navigation file includes the model with the three-dimensional boundary surface between the native bone surface and the osteophyte.

It is an object of the present invention to provide a process that provides for more accurate surgery.

It is another object of the present invention to provide a surgical process that achieves a satisfactory patient outcome.

It is another object the present invention to provide a surgical process that eliminates tolerance stacking.

It is another object of the present invention to provide a surgical process that reduces the time required for registration.

It is another object the present invention to provide a surgical process that reduces the workload of the surgeon.

It is another object of the present invention to provide a surgical process that directly measures the position of the bones of the knee.

It is another object of the present invention to provide a surgical process which avoids inaccurate measurements caused by tissues in the area of the knee.

It is a further object of the present invention to provide a surgical process that eliminates the need for independent optical, mechanical or radio frequency-based measurement of registration systems.

It is still further object of the present invention to provide a surgical process that eliminates line-of-sight issues.

These and other objects and advantages of the present invention will become apparent from a reading of the attached specification and appended claims.

BRIEF SUMMARY OF THE INVENTION

The present invention is a knee resurfacing process that comprises the steps of: (1) fixing a knee in a position; (2) creating an incision in the knee so as to expose a surface of the knee; (3) guiding a probe of a robot arm around a perimeter of a search zone on the surface of the knee; (4) probing the probe of the robot arm onto the knee so as to define a plurality of points within the perimeter; (5) collecting point cloud data from the plurality of points so as to form an image of the probed surface; and (6) shaping the knee relative to the collected point cloud data.

In the knee resurfacing process of the present invention, the step of fixing the knee comprises securing the knee to a fixture so that the femoral component and the tibial component of the knee are extended in an angular relationship.

The step of guiding includes hand guiding the probe so that the probe penetrates tissues at the bony surface of the knee and contacts a bone of the knee. The perimeter of the search zone is registered by actuating a trigger of the robot arm when the probe contacts the knee at the perimeter of the search zone. A force of the contact of the probe with the bone of the knee is then measured. In the preferred embodiment the present invention, the search zone will be a femoral articular surface of the knee.

In the process of the present invention, an image of the probe surface is compared with a three-dimensional model of the knee. The knee is imaged so as to create this three-dimensional model.

The step of probing includes probing the knee within the perimeter with a force corresponding to the measured force of the probe during the step of guiding. The step of shaping includes affixing a cutting tool to the robot arm and then moving the robot arm such that the cutting tool removes bone from the knee so that the knee is shaped so as to receive an implant thereon. The step of shaping further includes forming at least a first plane, a second plane and a third plane at the femoral articular surface of the knee.

In the present invention, the robot arm is from a multi-axis autonomous programmable robot. An amount of material to remove from the bone of the knee is determined based upon the image from the collected point cloud data. Ultimately, the implant is affixed to the shaped knee and the incision is then closed.

In robotic surgery, precise alignment of the robot relative the patient is essential for accurate surgery and satisfactory patient outcomes. The present invention improves accuracy, eliminates tolerance stack up, reduces the time required for registration of the anatomical features, and reduces the workload of the surgeon.

The present invention uses tactile sensing to directly measure the position of bones and other anatomical features. The surgeon uses collaborative hand-guiding of the robot arm to teach the perimeter of the search zone and the initial alignment points to the robot. Proprietary software running on a force-sensing collaborative robot then uses these boundaries to automatically probe the surface of interest with a combination of mechanical probes. The search pattern is optimized to ensure proper registration in a minimal amount of time.

The present invention uses either rounded or pointed probes. Rounded probes are used to sense soft tissues, while pointed probes penetrate soft tissue to detect bone therebeneath. Each type of probe uses a unique force detection level. This force level is programmable using software running on the collaborative robot. By probing to a specific force optimized for each type of anatomical structure, accurate registration is ensured on either soft or bony surfaces. As the robot collects point cloud data from the automated probing routine, these points are either used to create a three-dimensional model or to match an existing three-dimensional model created prior to surgery using CT, MRI or radiographic imaging. Once registration is complete, the robot uses this three-dimensional model and its position in space to accurately execute the surgical plan.

The approach of using a force-sensing collaborative robot for both registration and surgery eliminates the need for independent optical, mechanical or radio frequency-based measurement and registration systems. The single robot approach also eliminates tolerance stack-up and relative alignment issues which are inherent when using multiple systems. Robotic tactile sensing eliminates line-of-sight issues inherent to optical tracking systems. As such, the present invention improves on both accuracy, model matching and speed of registration of anatomical features.

This foregoing Section is intended to describe, with particularity, the preferred embodiments of the present invention. It is understood that modifications to these preferred embodiments can be made within the scope of the present claims. As such, this Section should not to be construed, in any way, as limiting of the broad scope of the present invention. The present invention should only be limited by the following claims and their legal equivalents.

DETAILED DESCRIPTION OF THE INVENTION

Figure 4:
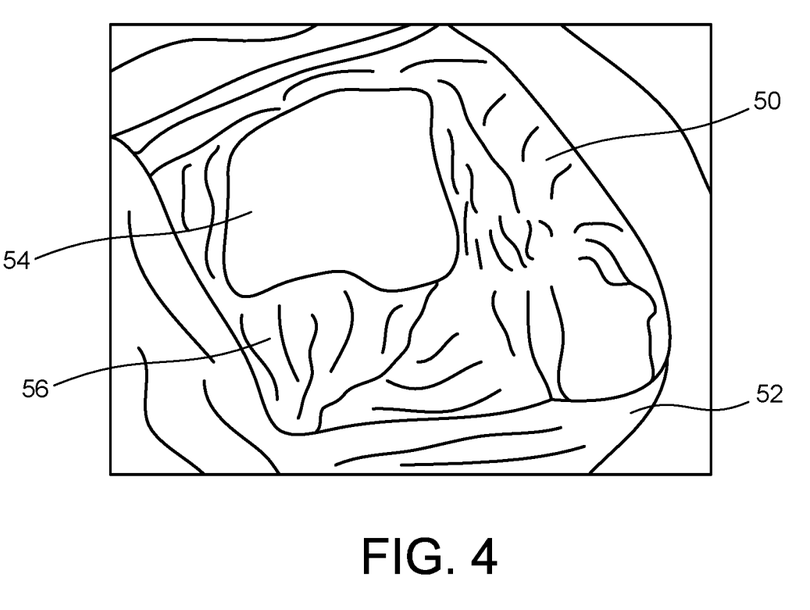
FIG. 4 is a plan view showing the opening of an incision to the femoral component of the knee in accordance with the present invention.

FIG. 4 shows an initial step in the process in the knee replacement process of the present invention. In FIG. 4, it can be seen that there is an incision 50 that is formed at the knee 52 so as to expose the femoral surface 54. Typically, the knee will be placed into a fixture so that the femoral component is extended at an angle with respect to the tibial component. Also, the leg is extended so as to generally move the particular tibial surface slightly away from the articular femoral surface.

In FIG. 4, it can be sheet seen that there are a wide variety of tissues 56 located in the area of the femoral surface 54. In conventional applications in the past, these tissues 56 would reside in close proximity to the femoral surface 54 during imaging. As such, CT or MRI imaging could produce an inaccurate image of the femoral surface 54. As such, the replacement surgery, in particular the resurfacing of the femoral articular surface, had to be carried out with guesswork. As such, a need has developed whereby the contour and shape of the femoral surface 54 can be determined without the need for imaging or can be more accurately ascertained in combination with imaging.

Figure 5:
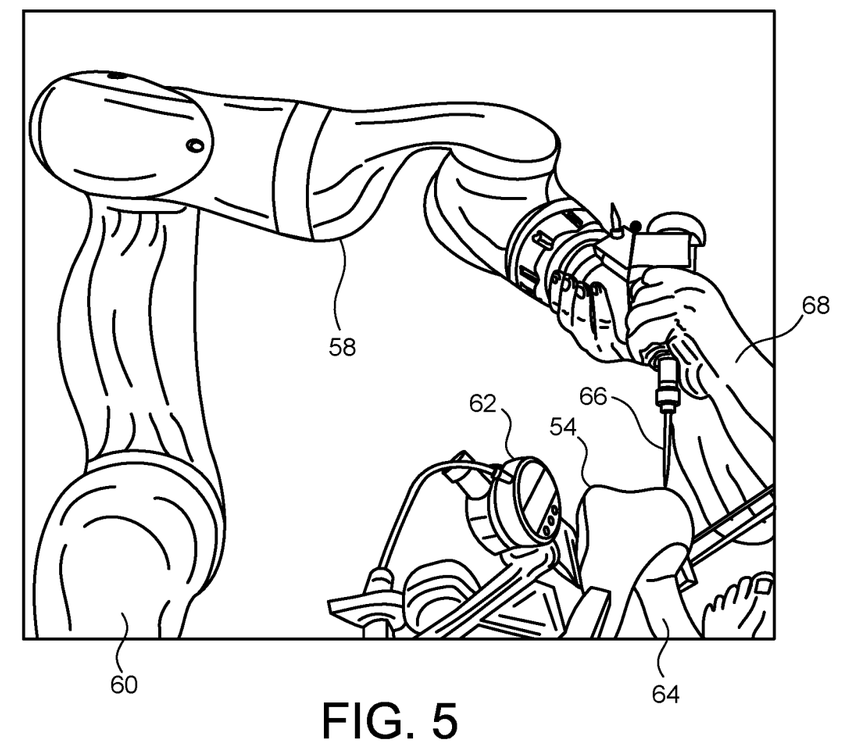
FIG. 5 is a illustration showing the guiding of the probe around the perimeter of the search zone in accordance with the present invention.

FIG. 5 shows an early step in the process of the present invention. As can be seen, there is a robot arm 58 that is supported from a fixed position 60. The femoral surface 54 is exposed (in the manner shown in FIG. 4). In particular, there is a fixture 62 that is secured to the femur and tibia of the leg 64 of the patient. This fixture 62 maintains the femoral surface 54 in a fixed position.

In the step shown in FIG. 5, it is important that the robot arm 58 register the exact position of the probe 66 from the base 60. In order for the robot arm 58 to know the exact position of the femoral surface 54 and the area of probing, it is necessary to establish the perimeter of a search zone for the robot arm 58. As such, person 68 manually manipulates the probe 66 around the perimeter of the search zone of the femoral surface 54. In particular, the person 68 applies a suitable pressure onto the probe 66 so as to penetrate the soft tissues adjacent to the femoral surface 54 and to directly contact the bone of the femoral surface 54. As such, the exact contour of the femoral surface 54 is measured. The present invention avoids the possibility of inaccurate measurements caused by interference from the tissues adjacent to the femoral surface 54. The person 68 will continually move the probe 66 to various points around a search zone on the femoral surface 54. A trigger on the probe 66 and the robot arm 58 is used so as to register each of the points around the perimeter. Typically, ten to twenty perimeter points can be registered around the search zone. This teaches the robot arm 58 the area in which to probe. The robot arm 58 is a 7 degree of freedom Kuka robot. In particular, this robot is considered to be a multi-axis autonomous programmable robot. The step of using the probe 66 to establish the perimeter of the search zone educates the robot where the femoral surface 54 is in relation to the base 60 of the robot. As such, the robot will know to move with the probe only within the perimeter established in the step shown in FIG. 5.

Figure 6:
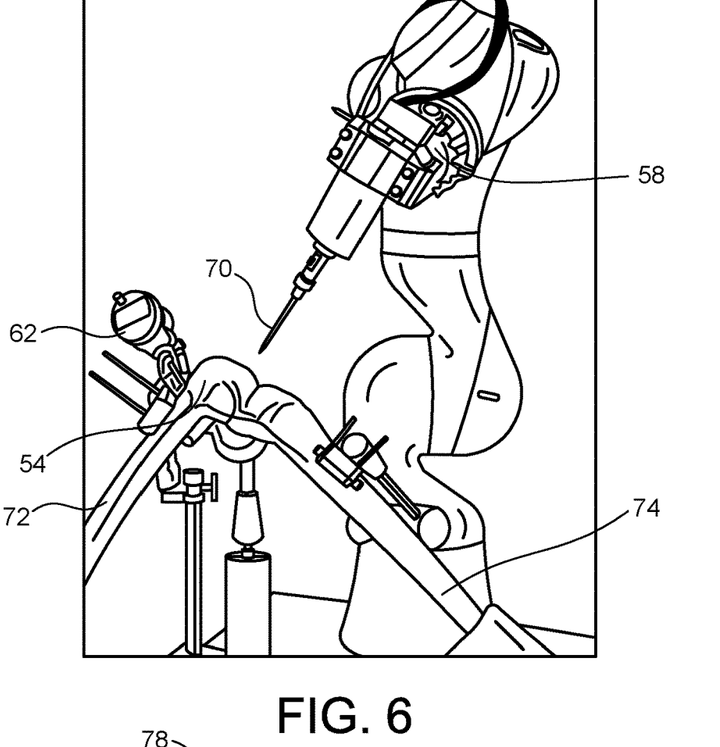
FIG. 6 is an illustration showing the probing of the femoral surface within the search zone in accordance with the present invention.

FIG. 6 shows the probing of the femoral surface 54 by a probe 70. FIG. 6 shows that the femur 72 extends at an angle with respect to the tibia 74. The fixture 62 fixes the position of the femur 72 and the tibia 74 so that the femoral surface 54 is exposed. Since the leg of the patient will always be in a fixed position and since the perimeter of the search zone is established through the steps of FIG. 5, the robot arm 58 will always be able to be directed toward the femoral surface 54. The probe 70 then proceeds to establish a plurality of points within the perimeter. A large number of points are established by the probe 70 within the search zone. As such, probe 70 will be able to provide feedback as to the actual contour of the femoral surface 54 within the search zone. Suitable software will process these point measurements so as to collect point cloud data from the plurality of points so as to form an image of the probe surface. It should be noted that force measurements can be made by the robot arm 58 from the probe 66 as shown in the step of FIG. 5. The robot arm 58 can manipulate the probe 70 so as to use similar forces so as to probe within the search zone of the femoral surface 54. As such, the probe 70 will be assured of suitably penetrating the soft tissues surrounding the femoral surface 54.

Figure 7:
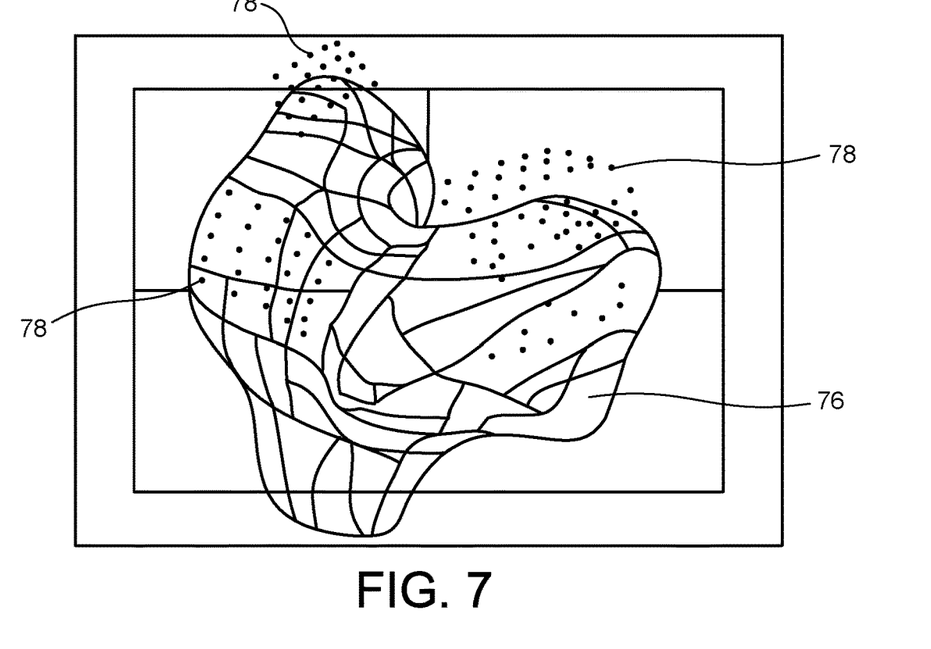
FIG. 7 illustrates the data obtained within the search zone relative to a three-dimensional model of the femoral surface in accordance with the present invention.

FIG. 7 shows that there is a three-dimensional model 76 of the femoral surface. The plurality of point measurements 78 from the probe 70 are illustrated as superimposed upon the three-dimensional model 76. The point measurements 78 can be suitably imaged so as to provide a surgeon with a very accurate image of the contours of the femoral surface 54. This can be carried out without the need for imaging equipment. Suitable processing of the point measurements 78 (in a type of connect-the-dots manner) will provide a clear image of the shape and size of the actual femoral surface 54. The surgeon can then use the image produced by the point cloud data of point measurements 78 to ascertain the amount of cutting required in order to form the planar surfaces necessary for the receipt of the implant onto the femoral surface.

Figure 8:
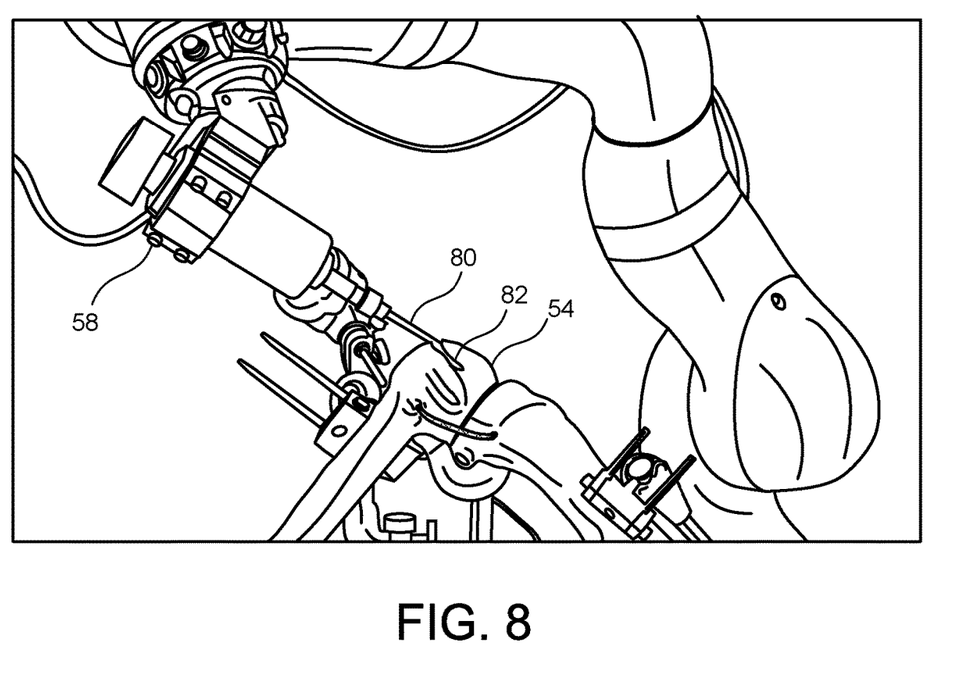
FIG. 8 shows the formation of one planar surface on the femoral surface in accordance with the present invention.

FIG. 8 shows that the robot arm 58 has a shaping tool 80 affixed thereto. Shaping tool 80 can have a milling end or similar type of tool so as to form a first planar surface 82 at the femoral surface 54. This can correspond to the planar surface 24 (as shown in FIG. 1). Since the exact shape of the femoral surface 54 is known by virtue of the point cloud data (shown in FIG. 7) obtained from the step of FIG. 6, the robot arm 58, once programmed for the desired depth of cut by the surgeon, will create a very accurate and repeatable shaping of the first planar surface 82. The only judgment call that is required of the surgeon during this process will be the depth of cut to receive the implant. The point cloud data (shown in FIG. 7) can be compared with image data so as to confirm the measurements carried out by the robot arm.

Figure 9:
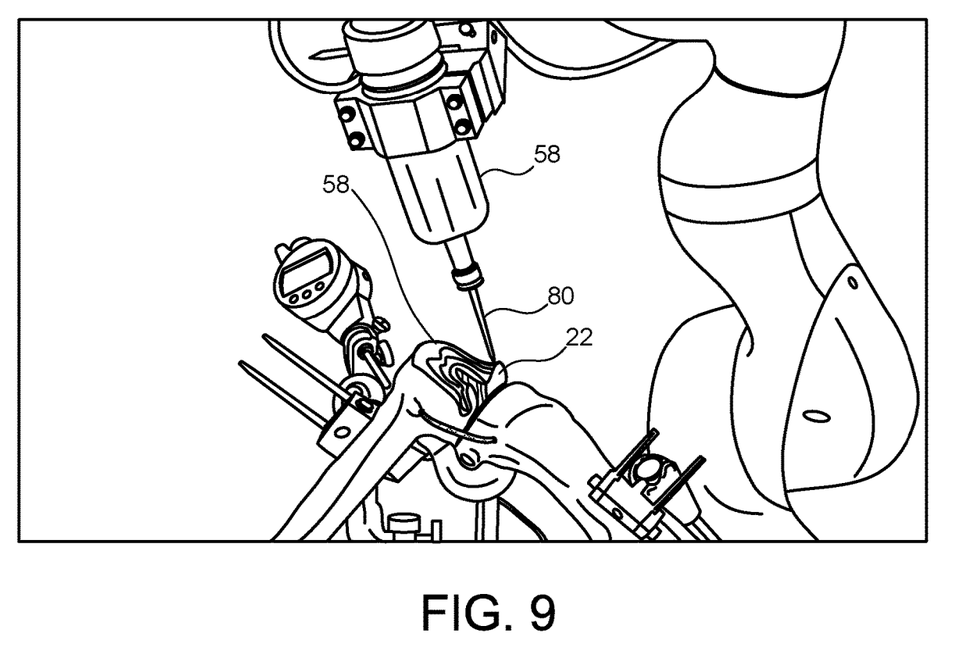
FIG. 9 shows the formation of the second planar surface on the femoral surface in accordance with the present invention.

FIG. 9 shows that the shaping tool 80 of the robot arm 58 has moved so as to create the second planar surface 22 at the femoral surface 58. Since the position of the shaping tool 80 is accurately known by the robot arm 58, the distance of the second planar surface 22 from the beginning of the shaping of the first planar surface 22 is known. This can correspond to the length of the corresponding surface on the prosthetic component 10. As such, a very accurate matching of the first planar surface to the second planar surface can be obtained. The length and width of the second planar surface 22 is known by virtue of the configuration of the notch 28 of the selected prosthetic component 10. As such, the robot 58 can be suitably programmed so as to shape the femoral surface 58 corresponding to the length and width of the corresponding surface of the prosthetic component 10.

Figure 10:
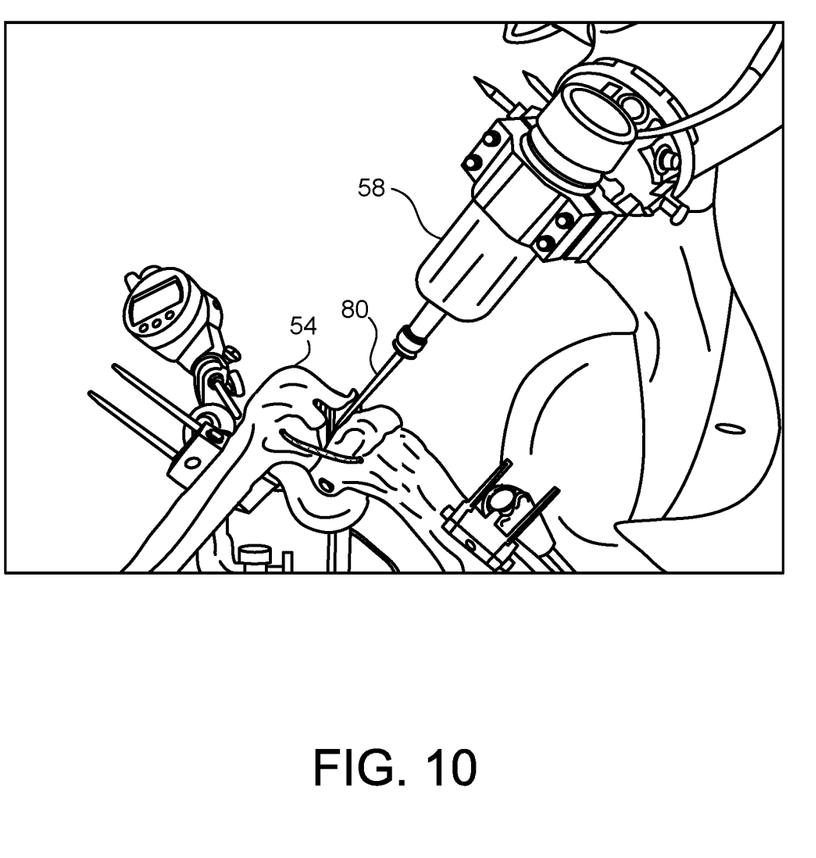
FIG. 10 illustrates the shaping of the third planar surface on the femoral surface in accordance with the present invention.

FIG. 10 shows a further step in the process of the present invention. In FIG. 10, a robot arm 58 is moved to an edge of the second planar surface. The shaping tool 80 is then used so as to form the third planar surface 20 (with reference to FIG. 1). Once again, since the length of the corresponding surface of the prosthetic component 10 is known, the robot arm 58 can be suitably programmed so as to assure that this third planar surface corresponds to and is complementary with the corresponding surface of the prosthetic component 10. As such, the complete shaping of the femoral surface 54 is generally completed through the use of the shaping tool 80 in combination with the robot arm 58. If necessary, a drilling tool can be utilized with the robot arm 58 so as to form the holes 30 associated with the pins 32 on the prosthetic component 10. If necessary, other surfaces can be also formed in the manner described herein previously.

It is to be noted that the process the present invention is particularly associated with the femoral surface of the knee replacement surgery. It is within the concept of the present invention that the robotic arm, and associated probes and shaping tools, can also be used in association with the formation of the tibial surface. In all circumstances, accurate measurements are achieved by the use of the probe within the search zone established by the hand-guided probe. As such, accurate assessments of the shape of the tibial component can be made available to the surgeon.

The present invention assures that there is precise alignment of the robot relative to the patient. This assures that accurate surgery is carried out and that there are satisfactory patient outcomes. The present invention improves accuracy, eliminates tolerance stack up, reduces the time required for registration of anatomical features, and reduces the workload of the surgeon.

The present invention uses tactile sensing to directly measure the position of the bones and other anatomical features. The surgeon uses collaborative hand guiding of the robot arm to teach the perimeter of the search zone and the initial alignment points to the robot. Software can be used in association with a force-sensing collaborative robot to use these boundaries to automatically probe the surface of interest. A combination of mechanical probes can be used. The search pattern is optimized to ensure proper registration in a minimal amount of time. The present invention can utilize either rounded or pointed probes. Rounded probes are used to sense soft tissues while pointed probes penetrate soft tissue to detect bone therebeneath. Each type of probe uses a unique force detection level. This force level is programmable using software running on the collaborative robot. By probing to a specific force optimized for each type of anatomical structure, accurate registration is ensured on either soft or bony surfaces. The robot collects point cloud data from the automated probing routine. These points are used to either create a three-dimensional model or to be matched to an existing three-dimensional model created prior to surgery using CT, MRI or radiographic imaging. Once registration is complete, the robot uses this three-dimensional model and its position in space to accurately execute the surgical plan.

This approach of using a force-sensing collaborative robot for both registration and surgery eliminates the need for independent optical, mechanical or radio frequency-based measurement and registration systems. The single robot approach also eliminates tolerance stack-up and relative alignment issues which are inherent when using multiple systems. The robotic tactile sensing eliminates line-of-sight issues inherent to optical tracking systems. As such, the present invention approves on accuracy, model matching and speed of registration of anatomical features.

The foregoing disclosure and description of the invention is illustrative and explanatory thereof. Various changes in the details of the described steps of the process can be made within the scope of the appended claims without departing from the true spirit of the invention. The present invention should only be limited by the following claims and their legal equivalents.

We claim:

1. A knee resurfacing process comprising:
   fixing a knee in a position;
   creating an incision in the knee so as to expose a bone surface of the knee;
   hand guiding a probe of a robot arm around a perimeter of a search zone on the bone surface of the knee such that the probe penetrates tissues at the bone surface and physically contacts the bone surface;
   probing the probe of the robot arm onto the bone surface of the knee such that the probe physically contacts the bone surface so as to define a plurality of points within the perimeter;
   collecting point cloud data from the plurality of points so as to form an image of the probed surface; and
   shaping the bone surface of the knee relative to the collected point cloud data.

2. The knee resurfacing process of claim 1, the step of fixing the knee comprising:
   securing the knee to a fixture so that a femoral component and a tibial component of the knee are extended in an angular relationship.

3. The knee resurfacing process of claim 1, the step of hand guiding comprising:
   registering the perimeter of the search zone by activating a trigger of the robot arm when the probe contacts the bone surface of the knee at the perimeter of the search zone.

4. The knee resurfacing process of claim 1, the search zone being a femoral articular surface.

5. The knee resurfacing process of claim 1, further comprising:
   comparing the image of the probed surface with a three-dimensional model of the knee.

6. The knee resurfacing process of claim 5, further comprising:
   imaging the knee so as to create the three-dimensional model.

7. The knee resurfacing process of claim 1, the step of shaping comprising:
   affixing a cutting tool to the robot arm; and
   moving the robot arm such that the cutting tool removes bone from the bone surface of the knee so that the bone surface is shaped so as to receive an implant.

8. The knee resurfacing process of claim 7, the step of shaping further comprising:
   forming at least a first plane and a second plane and a third plane at the femoral articular surface of the knee.

9. The knee resurfacing process of claim 1, the robot arm being from a multi-axis autonomous programmable robot.

10. The knee resurfacing process of claim 1, further comprising:
    determining an amount of bone to remove from the bone surface of the knee based on the image formed from the collected point cloud data.

11. The knee resurfacing process of claim 1, further comprising:
    affixing an implant to the shaped bone surface of the knee; and
    closing the incision.

12. A knee resurfacing process comprising:
    fixing a knee in a position;
    creating an incision in the knee so as to expose a bone surface of the knee;
    hand guiding a probe of a robot arm around a perimeter of a search zone on the bone surface of the knee such that the probe penetrates tissues at the bone surface and physically contacts the bone surface, the step of guiding a probe comprising:
       measuring a force of the contact of the probe with the bone surface of the knee;
    probing the probe of the robot arm onto the bone surface of the knee such that the probe physically contacts the bone surface with a force equal to the measurement force so as to define a plurality of points within the perimeter;
    collecting point cloud data from the plurality of points so as to form an image of the probed surface; and
    shaping the bone surface of the knee relative to the collected point cloud data.

* * * * *